United States Patent [19]
Duffy et al.

[11] Patent Number: 4,824,071
[45] Date of Patent: Apr. 25, 1989

[54] AN APPARATUS USED TO FABRICATE A CUSTOM FEMALE URINE COLLECTION DEVICE

[75] Inventors: Karen Duffy, Devon; Helfer, Joel, Chesire; Terese Campion, Waterbury, all of Conn.

[73] Assignee: Chesebrough-Pond's, Inc., Greenwich, Conn.

[21] Appl. No.: 65,325

[22] Filed: Aug. 6, 1987

Related U.S. Application Data

[62] Division of Ser. No. 628,463, Jul. 6, 1984, abandoned.

[51] Int. Cl.⁴ .................. B29C 39/24; B29C 39/26
[52] U.S. Cl. .................. 249/117; 249/55; 249/105; 425/542
[58] Field of Search .............. 249/55, 117, 105, 134; 264/222; 425/542

[56] References Cited

U.S. PATENT DOCUMENTS

| | | | |
|---|---|---|---|
| 2,147,707 | 2/1939 | Koehler | 249/55 |
| 3,528,423 | 9/1970 | Lee | 604/329 |
| 3,646,929 | 3/1972 | Bonnar | 600/29 |
| 3,661,155 | 5/1972 | Lindan | 604/329 |
| 3,683,914 | 8/1972 | Crowley | 604/329 |
| 3,705,575 | 12/1972 | Edwards | 600/29 |
| 3,776,235 | 12/1973 | Ratcliffe et al. | 604/329 |
| 3,800,800 | 4/1974 | Garbe et al. | 128/788 |
| 3,995,329 | 12/1976 | Williams | 604/329 |
| 4,019,498 | 4/1977 | Hawtrey et al. | 600/29 |
| 4,139,006 | 2/1979 | Corey | 600/29 |
| 4,194,508 | 3/1980 | Anderson | 604/329 |
| 4,246,901 | 1/1981 | Michaud | 604/329 |
| 4,280,498 | 7/1981 | Jensen | 604/335 |
| 4,296,502 | 10/1981 | Bortle | 4/144.1 |
| 4,401,534 | 8/1983 | Goepp et al. | 264/222 |
| 4,457,314 | 7/1984 | Knowles | 128/760 |
| 4,496,355 | 1/1985 | Hall et al. | 604/327 |
| 4,530,810 | 7/1985 | Nemoto | 264/222 |
| 4,631,061 | 12/1986 | Martin | 604/329 |

FOREIGN PATENT DOCUMENTS 3006  2/1890  United Kingdom .............. 128/835

Primary Examiner—Willard Hoag
Attorney, Agent, or Firm—Brumbaugh, Graves, Donohue & Raymond

[57] ABSTRACT

An impression cup of a female unogenital region for use in fabricating a customized female urine receptacle and having a rim and connecting wall portions defining an opening sufficient to surround the urethral opening, the wall portion also having another opening for introducing an impression material into the receptacle and means suitable for introducing an impression material into the opening in the wall portion.

4 Claims, 3 Drawing Sheets

AN APPARATUS USED TO FABRICATE A CUSTOM FEMALE URINE COLLECTION DEVICE

This application is a division of application Ser. No. 628,468 filed on July 6, 1984. Which was abandoned in favor of continuation of application Ser. No. 045.702 filed Apr. 29, 1987.

BACKGROUND OF THE INVENTION

The present invention relates to an apparatus used to fabricate an improved urine collection system for females who are incontinent or who are unable to use ordinary restroom facilities for extended periods of time.

While the use of absorbent materials, e.g. pads and garments, and catheterization represent two frequently used methods for treating urinary incontinence in females, neither is suited for extended periods of time or for females who while suffering from urinary incontinence otherwise lead normal active lifestyles, or who as a result of occupational circumstances cannot avail themselves of ordinary restroom facilities.

Absorbent garments, e.g. adult diapers, and pads are bulky, uncomfortable and hygienically offensive. The garments or pads must be frequently changed since urine trapped within the absorbent material provides a natural medium for bacterial growth and may cause both irritation and infection of sensitive skin tissue. Moreover, because the garment or pad does not prevent urine from contacting the vaginal and urethral openings or interior thereof, particularly when worn by one who is bedridden, there is a relatively high risk of serious internal infection.

As an alternative, indwelling catheterization, while preventing tissue maceration, is nonetheless irritating, if not painful and may result in urinary tract infections and bladder irritation. Moreover, it is unsuitable for the generally active female, i.e. those not confined to bed, but who nonetheless suffer from urinary incontinence or who are unable to use ordinary restroom facilities due to occupational circumstances.

A third and perhaps the most effectively balanced approach to urinary incontinency involves the use of a cup-like receptacle which is designed and positioned so as to surround substantially the uro-genital region and to collect urinary discharge. These receptacles are generally formed with an opening in the bottom which is connected to a drainage tube for transporting the urine to a suitable collection means, for example bag, generally secured to the leg of the patient. The receptacles may vary in size so as to surround the entire uro-genital area or fit within the uro-genital area (between the labia major) and surround essentially the urethral opening. The former, or large variety of receptacle, is generally held in place by means of a vaginal insert member affixed to the receptacle and a supporting garment. The latter, or smaller sized receptacle may either be held in place by the labia major alone or in combination with an attached vaginal insert member, an adhesive and/or support garment.

With either variety of receptacle, urine leakage is a major problem principally attributable to the inability of these devices to effect an essentially leak-resistant seal between the rim of the receptacle and the vulvar tissue which it contacts. All of the known urine receptacle devices are formed with generally smooth rim portions which do not mate well with the highly irregular and individual surface contours of the uro-genital tissue. While it is taught in the prior art to fabricate receptacles from materials such as ethyl methacrylate which becomes pliant at ordinary body temperatures and pressures so as to conform to the configuration of the user's body, in fact an optimum seal is not obtained and urine leakage continues to be a major problem along with the associated problems of vaginal infections and skin irritation.

These problems are substantially eliminated by the present invention which provides for a novel process of making a customized urine receptacle, the rim of which is fabricated to mate with the precise surface contours of the uro-genital tissue which it contacts.

Apart from the foregoing object of providing an essentially leak proof urine receptacle, it is a further object of the present invention to provide a urine collection device that does not utilize a vaginal insert member, but which may be easily and comfortably positioned with reference to the anterior wall of the vaginal opening, thereby permitting the simultaneous use of tampons during menstruation.

Still other objects, features and advantages of the present invention will be made apparent by the following description of preferred embodiments, drawings and claims.

DESCRIPTION OF THE PREFERRED EMBODIMENTS

Figure 1:
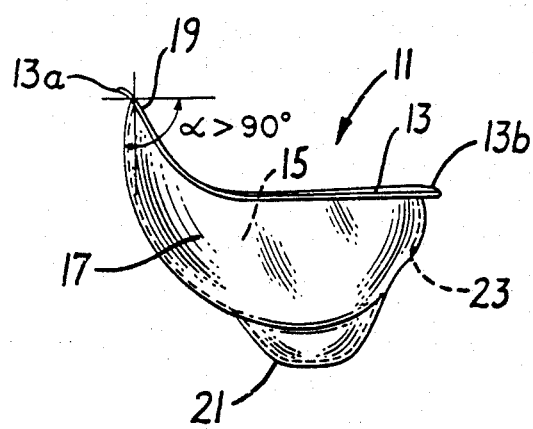
FIG. 1 is a side view of an impression cup.
Figure 2:
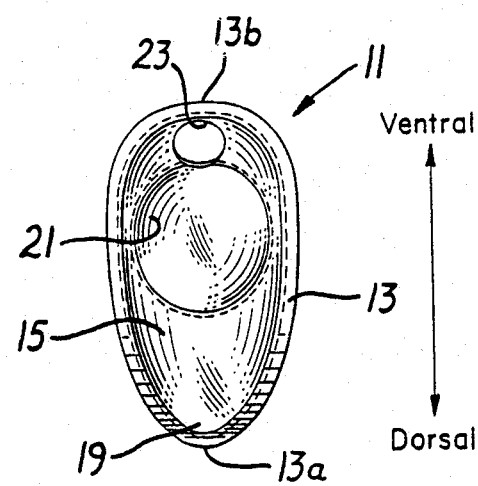
FIG. 2 is a plan view of the impression cup of FIG. 1.

In accordance with a preferred embodiment of the process of the present invention, an impression of the urethral opening and other selected portions of the urogenital region of the patient is taken by placing the impression cup of FIG. 1 over the vulvar region. The impression cup 11 has a generally semi-ovoid shape. A rim portion, 13 which defines opening 15, is connected to generally concave, substantially rigid thin wall surfaces 17. With reference to the cup position when taking an impression of the urogenital area, i.e. with the cup oriented in a generally ventral-dorsal direction (FIG. 2), the dorsal end 19 of cup 11 is tapered and curved downwardly slightly more than about 90° (see reference angle of FIG. 1) in order to conform substantially to the natural arch of the vulvar anatomy between the urethral orifice and the anterior surface of the entrance to the vaginal opening. The top, outer wall of cup 11 is formed with a generally semi-spherical protuberance 21 and opening 23 located on the ventral side wall. The cup 11, which may be fabricated in a variety of standard sizes, is made of any suitable and preferably translucent plastic material.

In accordance with the impression taking phase of the process, a patient is placed on an examining table in the standard gynecological examining position. The labia (major and minor) are spread and the urethral orifice is located. A proper sized impression cup 11, i.e. suitable to the patient's vulvar anatomy, is selected and cup opening 15 is placed over the urethral orifice in such a manner that the tapered and curved dorsal rim portion 13a contacts the anterior surface of the entrance to the vaginal orifice but so as not to interfere with, i.e. obstruct, the vaginal sphincter.

In positioning the cup, it is important that the vulvar tissues not be distorted. Moreover, proper size selection and placement of the cup are critical to insure the fabrication of an essentially leak-proof urine receptacle. In this regard, it has been found that the inside rim of the cup should be located at least about 1.3 cm (0.5") from the urethral orifice on all sides.

Figure 3:
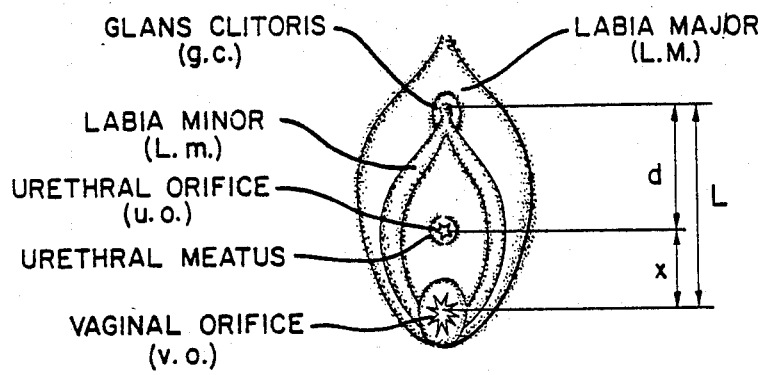
FIG. 3 is a schematic rendering of the vulvar (urogenital) area.

With reference to FIG. 3, the following cases describe two preferred positions in which the impression cup may be placed to obtain a proper impression.

CASE I

The distance from the vaginal orifice to the glans clitoris is less than about 4 cm (L) and the urethral orifice is located between said anatomy. The cup size is chosen so as to fit interiorly of the labia major, with the ventral end of the cup rim 13b of FIG. 2 extending over the ventral portion of the labia minor and glans clitoris and the tapered dorsal end of the cup rim 13a positioned inward of the dorsal portion of the labia minor and terminating at the anterior surface of the vaginal entrance. In this position, the labia major should fold comfortably over the outer wall surface of the cup.

CASE II

The distance from the vaginal orifice to the glans clitoris (L) is larger than 4 cm and the urethral orifice is at least 1.5 cm from the glans clitoris (d). The cup size is chosen so as to fit comfortably interiorly of the labia minor with the tapered dorsal rim end 13a of cup 11 terminating at the anterior surface of the vaginal entrance. In this position, the labia major and minor should fold comfortably over the outer wall surface of the cup 11.

With the impression cup firmly positioned as described in Case I or Case II, and so as not to distort the vulvar tissue, a physiologically suitable impression material is syringed into the cup through the ventral side wall opening 23. The amount of impression forming material syringed into the cup should be sufficient to completely fill the cup, i.e. material should begin to emerge from the rim of the cup, and no air pockets should be visible. When the cup is filled, the syringe (not shown) is removed and the cup is held in position until the impression material hardens into a form retaining structure. Thereafter the cup is removed from the patient and the impression structure is removed from the cup and washed in warm soapy water.

Figure 4:
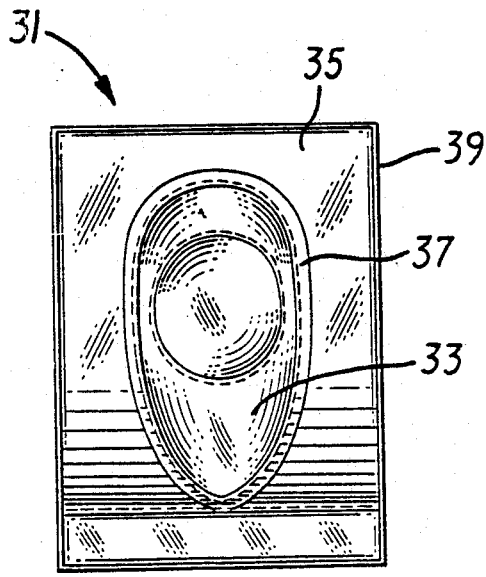
FIG. 4 is a plan view of an impression holder.
Figure 5:
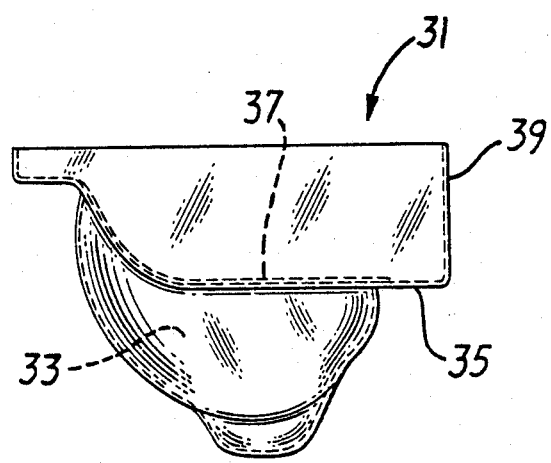
FIG. 5 is a side view of the impression holder of FIG. 4.

The impression structure is then placed into a holding means 31 illustrated in FIGS. 4 and 5 for further processing. Said holding means is formed with a cavity 33, the interior surface configuration of which matches the configuration of the wall surface 17 of the impression cup 11 and corresponding impression structure. A flange portion 35 extends substantially laterally from the rim 37 of the cavity and terminates in substantially perpendicular wall portions 39 to provide a trough-like receptacle. The holding means may be prefabricated from any suitable material in a variety of standard sizes, compatible with the variety of standard sized impression cups.

Figure 6:
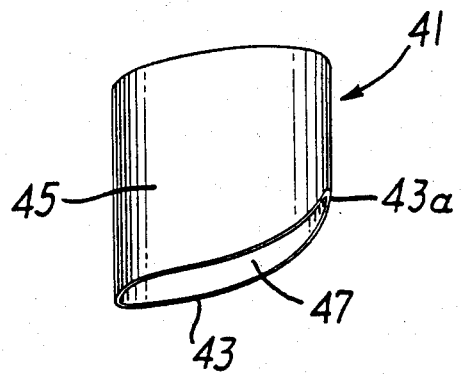
FIG. 6 is a perspective view of a cutting tool.
Figure 7:
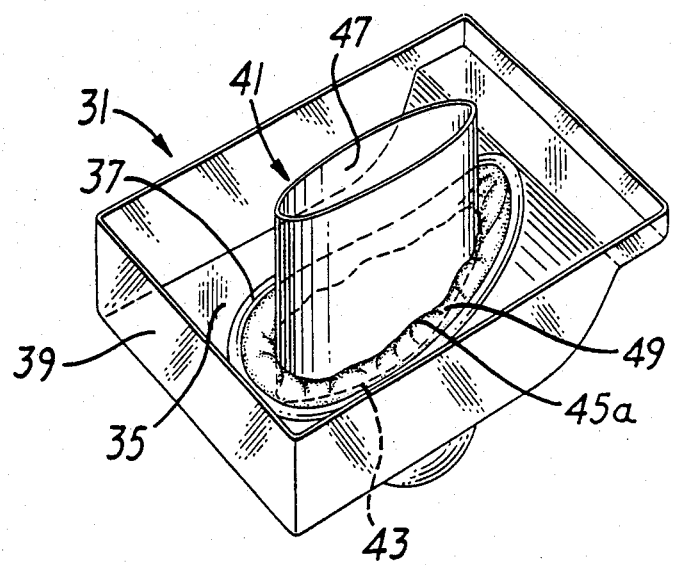
FIG. 7 is a perspective view of the cutting tool of FIG. 6 with the cutting edge embedded in an impression held within holder of FIG. 4.
Figure 8:
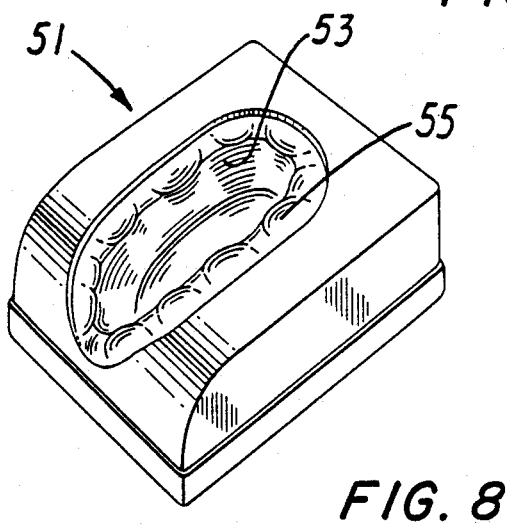
FIG. 8 is a perspective view of a mould formed from the arrangement of elements illustrated in FIG. 7.

With the impression structure firmly secured within the cavity of the holding means 31, a cutting tool 41 substantially, as depicted in FIG. 6, is inserted into the exposed (top) surface of the impression structure. The cutting tool has a generally ovoid-shaped cutting edge 43 and connecting wall portions 45 which define a hollow center area 47. One end of the cutting edge 43a is curved upwardly, i.e. in a direction substantially transverse to the plane of the cutting edge. The design of the cutting edge 43 of the tool is smaller but otherwise similar to the generally elliptical top surface of the impression structure, thereby permitting the cutting edge to be inserted inwardly of the edge of the impression structure When tool 41 is inserted into the top surface of the impression structure, as shown in FIG. 7, the hollow center area 47 of tool 41 surrounds a corresponding center area on the impression structure. The outer wall surface 45a of tool 41 defines a rim portion 49 on the impression structure surface, the thickness of which ranges from about $\frac{1}{8}$" to about $\frac{3}{8}$". The cutting tool may be prefabricated from any suitable material in a variety of standard sizes compatible with the variety of standard-sized impression cups. It will be understood by those skilled in the art that the cutting tool can be constructed in two parts and the cuts made sequentially The impression holding means 31, which now contains the impression structure with the cutting edge 43 of tool 41, or a replica thereof, embedded into its top surface, is then filled with a suitable moulding compound, e.g. plaster of paris to form a mould 51 substantially as depicted in FIG. 8. The mould has a central cavity portion 53 formed by the wall surface 45a of tool 41 which projects above the top surface of the impression structure, and a rim portion 55 which replicates the surface contours corresponding to the patient's vulvar region as dictated by the impression thereof formed on the surface of the impression structure.

Figure 9:
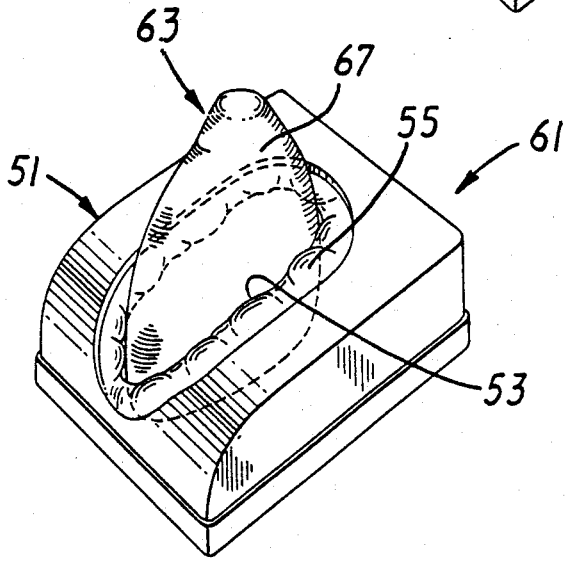
FIG. 9 is a perspective view of the mould of FIG. 8 and an insert member.
Figure 10:
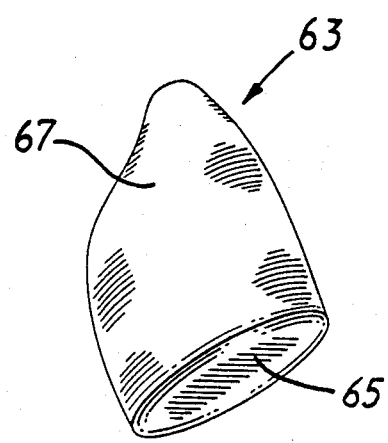
FIG. 10 is a perspective view of the insert member of FIG. 9.

The plaster mould 51 is removed from the impression holding means 31, and an insert member is securely positioned within the cavity portion 53 of the mould to form a mould assembly 61 as depicted in FIG. 9. The insert 63, shown in FIG. 10, has a bottom portion 65, configured to fill the mould cavity 53 and a top portion 67 configured to define the interior wall surface of the final urine collection receptacle. The insert member may be prefabricated from any suitable material, for example plaster, and in a variety of standard sizes.

Figure 11:
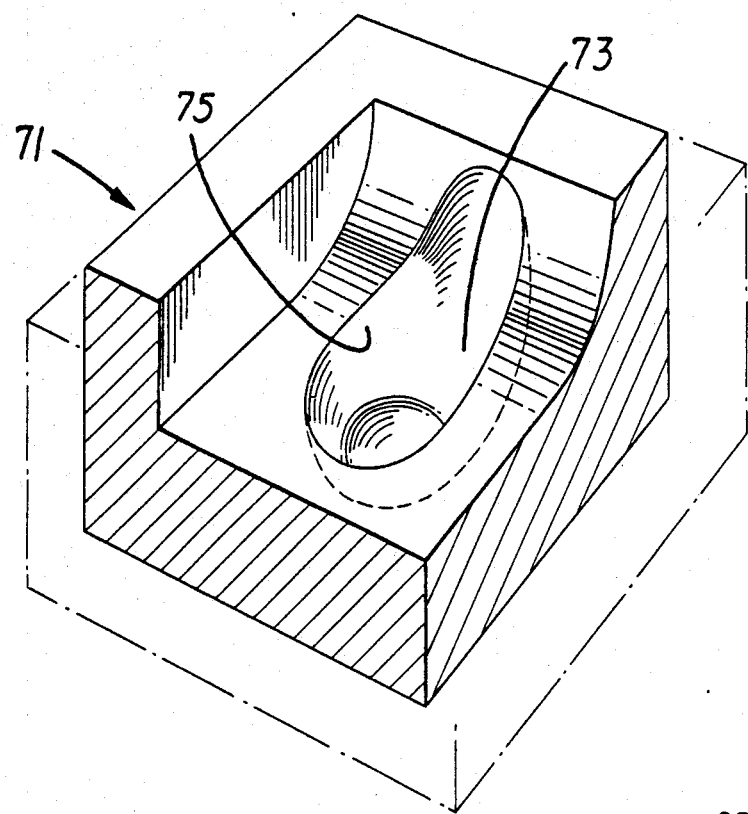
FIG. 11 is a perspective, partially cut away view of a receiving mould element.

The mould assembly 61 is thereafter inserted into a receiving mould 71 containing a fluid material suitable for forming the final urine collection receptacle such as ethyl methacrylate or a medical grade silicone. The receiving mould 71 (depicted in FIG. 11) is formed with a cavity 73, the wall surface 75 which defines the outer wall of the final urine collection receptacle. The receiving mould may also be prefabricated from any suitable material, and in a variety of standard sizes compatible with the variety of standard-sized impression cups.

The dimensions of the mould assembly 61 and mould receptacle 71 are such that when the two elements are joined together, i.e. by inserting the mould assembly into the mould receptacle, a space, preferably substantially equi-distant in all directions is formed between the cavity wall surfaces 75 in the mould receptacle and the exposed surface, i.e. top portion 67 of the insert 63. Upon inserting the mould assembly element 61 into the receiving mould element 71, the material for forming the final receptacle, present in the mould receptacle 71, flows into the space formed, thus forming the walls of the final urine collection receptacle.

Figure 12:
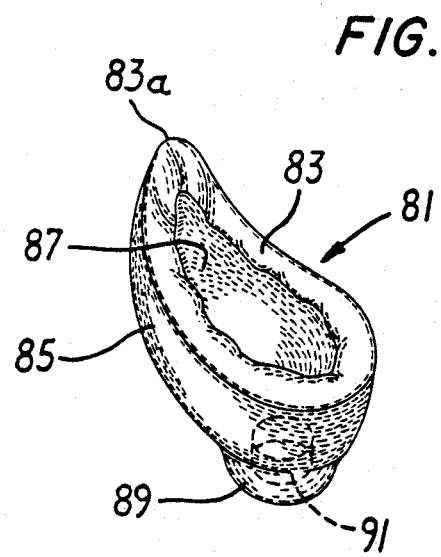
FIG. 12 is a perspective view of the final urine collection device.

When the final moulding compound has sufficiently solidified, the mould assembly 61 is removed from the mould receptacle 71 and the final urine collection receptacle 81, illustrated in FIG. 12 is removed.

Figure 13:
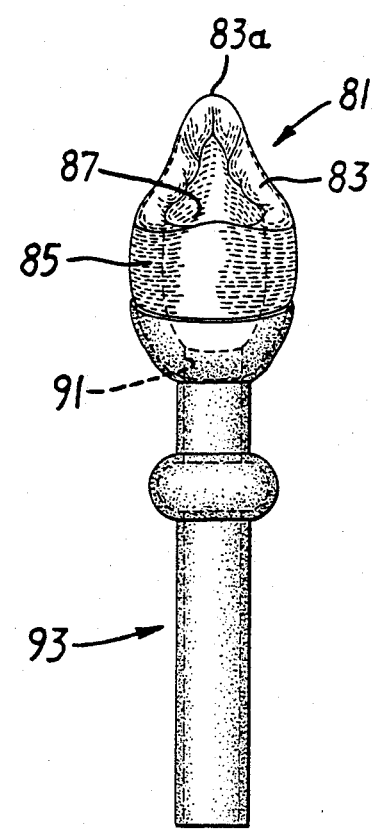
FIG. 13 is a front view of the final urine collection device of FIG. 12 and conduit means.

The final receptacle 81 (FIG. 12), fabricated in accordance to the foregoing procedures, has an essentially semi-ovoid shape, substantially identical to the impression cup 11. The rim portion 83 of the receptacle replicates the rim portion of the impression structure and when worn mates with the corresponding rim contours of the vulvar portion of the patient which it contacts. Rim 83 and connecting wall surfaces 85 define an ovoid-shaped opening 87 which surrounds, inter alia, the urethral opening. When worn by a female in a standing position (FIG. 13), the receptacle is oriented in a generally ventral-dorsal direction. The dorsal end of the rim and wall portions, respectively 83a and 85 of the receptacle, are tapered and curved upwardly slightly more than about 90° to conform to the natural arch of the vulvar anatomy between the urethral opening and the anterior surface entrance to the vaginal opening, but without being vaginally invasive.

Like the impression cup, the receptacle is formed with a semi-spherical, generally concave protuberance 89 located on the exterior bottom portion of wall surface 85. An opening 91 is formed in the bottom of said protuberance which communicates with the interior of the receptacle. A conduit or tube member 93 is adhesively secured to the exterior bottom portion so as to communicate with opening 91 formed therein, thereby providing means for transporting the urine from the receptacle to a collection means, which can be strapped to the user's leg.

The foregoing processing steps, apparatus and techniques are merely illustrative of those which are currently preferred; however, many modifications of said processing steps, apparatus and techniques will be obvious to those skilled in the art and hence, what is disclosed specifically is not intended in any way to limit the scope of the invention claimed hereinbelow.

We claim:

1. A device for taking an impression of the female urogenital region for use in fabricating a customized female urine receptacle comprising:
    a receptacle having a rim and connecting wall portions which together define an opening, said device when used being oriented generally in a ventral-dorsal direction, wherein the dorsal end of said receptacle is tapered and the dimensions of the receptacle are such that the device may be positioned interiorly of the labia major and the opening defined by the rim and wall portions being sufficient to surround the urethral opening; said device having an opening in the wall portion and means for introducing an impression forming material through said opening in the wall portion.

2. The device according to claim 1 wherein the configuration of the receptacle and opening therein is substantially semi-ovoid; and wherein the dorsal end is tapered and curved downwardly to conform to the natural arch of the vulvar anatomy between the urethral opening and the anterior wall surface of the vaginal opening.

3. The device according to claim 1 wherein the dorsal end is substantially vaginal non-invasive.

4. The device according to claim 3 wherein the dorsal end is tapered and curved downward more than 90°.

* * * * *